United States Patent
First

(10) Patent No.: US 7,419,675 B2
(45) Date of Patent: Sep. 2, 2008

(54) METHOD FOR TREATING PERITONEAL ADHESIONS

(75) Inventor: Eric R. First, Boston, MA (US)

(73) Assignee: Allergan, Inc., Irvine, CA (US)

( * ) Notice: Subject to any disclaimer, the term of this patent is extended or adjusted under 35 U.S.C. 154(b) by 354 days.

(21) Appl. No.: 11/139,318

(22) Filed: May 26, 2005

(65) Prior Publication Data

US 2006/0269573 A1   Nov. 30, 2006

(51) Int. Cl.
 *A61K 39/02* (2006.01)
 *A61K 39/00* (2006.01)
 *A61K 39/08* (2006.01)
 *A61K 38/00* (2006.01)

(52) U.S. Cl. .............. 424/236.1; 424/184.1; 424/234.1; 424/247.1; 530/300

(58) Field of Classification Search .............. 424/184.1, 424/236.1, 239.1, 247.1
See application file for complete search history.

(56) References Cited

U.S. PATENT DOCUMENTS

| | | | |
|---|---|---|---|
| 5,437,291 A | 8/1995 | Pasricha et al. | 128/898 |
| 5,670,484 A | 9/1997 | Binder | 514/14 |
| 5,714,468 A | 2/1998 | Binder | 514/14 |
| 5,766,605 A | 6/1998 | Sanders et al. | 424/239.1 |
| 5,989,545 A | 11/1999 | Foster et al. | 424/183.1 |
| 6,063,768 A | 5/2000 | First | 514/14 |
| 6,113,915 A | 9/2000 | Aoki et al. | 424/236.1 |
| 6,139,845 A | 10/2000 | Donovan | 424/236.1 |
| 6,143,306 A | 11/2000 | Donovan | 424/236.1 |
| 6,261,572 B1 | 7/2001 | Donovan | 424/239.1 |
| 6,265,379 B1 | 7/2001 | Donovan | 514/14 |
| 6,299,893 B1 | 10/2001 | Schwartz et al. | 424/422 |
| 6,306,423 B1 | 10/2001 | Donovan et al. | 424/423 |
| 6,312,708 B1 | 11/2001 | Donovan | 424/423 |
| 6,358,917 B1 * | 3/2002 | Carruthers et al. | 514/2 |
| 6,365,164 B1 | 4/2002 | Schmidt | 424/239.1 |
| 6,423,319 B1 | 7/2002 | Brooks et al. | 424/239.1 |
| 6,447,787 B1 | 9/2002 | Gassner et al. | 424/247.1 |
| 6,458,365 B1 | 10/2002 | Aoki et al. | 424/239.1 |
| 6,464,986 B1 | 10/2002 | Aoki et al. | 424/239.1 |
| 6,623,742 B2 | 9/2003 | Voet | 424/236.1 |
| 6,667,041 B2 | 12/2003 | Schmidt | 424/239.1 |
| 6,787,517 B1 * | 9/2004 | Gil et al. | 514/1 |
| 2002/0177545 A1 | 11/2002 | Donovan | |
| 2003/0224019 A1 | 12/2003 | O'Brien | 424/239.1 |
| 2004/0009180 A1 | 1/2004 | Donovan | 424/184.1 |
| 2005/0123567 A1 | 6/2005 | First | 424/239.1 |

FOREIGN PATENT DOCUMENTS

| | | |
|---|---|---|
| DE | 198 52 981 | 11/1998 |
| WO | WO 96/33273 | 4/1996 |
| WO | WO 98/07864 | 8/1997 |
| WO | WO 99/17806 | 10/1998 |
| WO | WO 00/57897 | 3/1999 |
| WO | WO 00/10598 | 8/1999 |
| WO | WO 00/15245 | 9/1999 |
| WO | WO 00/74703 | 5/2000 |
| WO | WO 01/21213 | 9/2000 |
| WO | WO 03/011333 | 7/2002 |

OTHER PUBLICATIONS

Webster's II New Riverside University Dictionary, The Riverside Publishing Company, 1984.*
U.S. Appl. No. 10/814,764, filed Mar. 31, 2004, First.
U.S. Appl. No. 10/817,036, filed Apr. 2, 2004, First.
Aoki K., et al, *Mechanisms of the antinociceptive effect of subcutaneous Botox: Inhibition of peripheral and central nociceptive processing*, Cephalalgia Sep. 2003;23(7):649.
Asahina A., et al., *Specific induction of cAMP in Langerhans cells by calcitonin gene-related peptide: relevance to functional effects*, Proc Natl Acad Sci U S A. Aug. 29, 1995;92(18):8323-7.
Bhutani M.S., et al., *Botulinum toxin injection in achalasia before myotomy*, Am J Gastroenterol Jun. 1998;93(6):1012.
Bigalke H., et al., *Botulinum A Neurotoxin Inhibits Non-Cholinergic Synaptic Transmission in Mouse Spinal Cord Neurons in Culture*, Brain Research 360;318-324:1985.
Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981.
Binz T. et al., *The Complete Sequence of Botulinum Neurotoxin Type A and Comparison with Other Clostridial Neurotoxins*, J Biological Chemistry 265(16);9153-9158:1990.
Boyd, *Mov Disord*, 10(3):376:1995 (pancreatic islet B cells contains at least SNAP-25 and synaptobrevin).
Brem, H., et al, *Placebo-Controlled Trial of Safety and Efficacy of Intraoperative Controlled Delivery by Biodegradable Polymers of Chemotherapy for Recurrent Gliomas*, Lancet 345;1008-1012:1995.

(Continued)

*Primary Examiner*—N. M. Minnifield
*Assistant Examiner*—Vanessa L. Ford
(74) *Attorney, Agent, or Firm*—Claude L. Nassif; Stephen Donovan; Martin Voet

(57) ABSTRACT

Methods for treating peritoneal adhesions by local administration of a Clostridial toxin, such as a botulinum toxin, to a patient with a peritoneal adhesion.

7 Claims, No Drawings

OTHER PUBLICATIONS

Bushara K., *Botulinum toxin and rhinorrhea*, Otolaryngol Head Neck Surg 1996;114(3):507.

Childers et al. (2002), American Journal of Physical Medicine & Rehabilitation, 81:751-759.

Chuang, et al., Intravesical botulinum toxin A administration produces analgesia against acetic acid induced bladder pain responses in rats, J Urol Apr. 2004;171(4 Suppl).

Doggweiler R., et al., *Botulinum toxin type A causes diffuse and highly selective atrophy of rat prostate*, Neurourol Urodyn 1998;17(4):363.

Eaker E. Y., et al., *Untoward effects of esophageal botulinum toxin injection in the treatment of achalasia*, Dig Dis Sci Apr. 1997;42(4):724-7 1012.

Ellis, H., The clinical significance of adhesions: focus on intestinal obstruction. *European Journal of Surgery*, Suppl (577), 5-9 (1997).

Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58;672-684:1998.

Goldman (2000), Aesthetic Plastic Surgery Jul.-Aug. 24(4):280-282.

Gonelle-Gispert, *Biochem J 1*;339 (pt 1):159-65:1999.

Gordon J.M., et al., *Prospective study of esophageal botulinum toxin injection in high-risk achalasia patients*, Am J Gastroenterol Oct. 1997;92(10):1812-7 1012.

Habermann E., et al., *Tetanus Toxin and Botulinum A and C Neurotoxins Inhibit Noradrenaline Release From Cultured Mouse Brain*, J Neurochem 51(2);522-527:1988.

Habermann E., *Inhibition by Tetanus and Botulinum A Toxin of the release of [3H]Noradrenaline and [3H]GABA From Rat Brain Homogenate*, Experientia 44;224-226:1988.

Habermann, *Naunyn-Schmiedeberg's Arch. Pharmacol.* 1974; 281, 47-56.

*Harrison's Principles of Internal Medicine* (1998), edited by Anthony Fauci et al., 14th edition, published by McGraw Hill.

Hokfelt T., *Neuropeptides in perspective : The last ten years*, Neuron 1991; 7: 867-879.

Hosoi J., et al., *Regulation of Langerhans cell function by nerves containing calcitonin gene-related peptide*, Nature. May 13, 1993;363(6425):159-63.

Hsieh S., et al., *Skin Innervation and Its Effects on the Epidermis*, J Biomed Sci. 1997;4(5):264-268.

Inaba N., et al., Capsaicin-induced calcitonin gene-related peptide release from isolated rat stomach measured with a new chemiluminescent enzyme immunoassay, Jpn J Pharmacol. Nov. 1996;72(3):223-9.

Jankovic J. et al., *Therapy With Botulinum Toxin*, Marcel Dekker, Inc., (1994), p. 5 and 150.

Johnson M., *Synaptic glutamate release by postnatal rat serotonergic neurons in microculture*, Neuron 1994; 12: 433-442.

Kaneko T., et al., *Immunohistochemical demonstration of glutaminase in catecholaminergic and serotonergic neurons of rat brain*, Brian Res. 1990; 507: 141-154.

Kasakov L., et al., *Direct evidence for concomitant release of noradrenaline, adenosine 5"-triphosphate and neuropeptide Y from sympathetic nerve supplying the guinea-pig vas deferens.* J. Auton. Nerv. Syst. 1988; 22: 75-82.

Kupfermann I., *Functional studies of contransmission*. Physiol. Rev. 1991; 71: 683-732.

Legat F., et al., *Repeated subinflammatory ultraviolet B irradiation increases substance P and calcitonin gene-related peptide content and augments mustard oil-induced neurogenic inflammation in the skin of rats*, Neurosci Lett. 2002 Sep. 6;329(3):309-13.

Lundberg J., *Pharmacology of cotransmission in the autonomic nervous system: Integrative aspects on amines, neuropeptides, adenosine triphosphate, amino acids and nitric oxide*, Pharmacol. Rev. 1996; 48: 113-178.

Menzies, D., et al., *Intestinal obstruction from adhesions—how big is the problem?*, Annals of the Royal College of Surgeons, England, 72, 60-63 (1990).

Moyer E et al., *Botulinum Toxin Type B: Experimental and Clinical Experience*, being chapter 6, pp. 71-85 of "Therapy With Botulinum Toxin", edited by Jankovic, J. et al. (1994), Marcel Dekker, Inc.

Naumann, *European J. Neurology* 6 (Supp 4): S111-S115:1999.

Nicholas A. et al., *Glutamate-like immunoreactivity in medulla oblogata catecholamine/substance P neurons*, NeuroReport 1990; 1: 235-238.

Nicholas A., et al., *Serotonin-, Substance P- and Glutamae/Aspartate-like Immunoreactivities in Medullo-Spinal Pathways of Rat and Primate*, Neuroscience, vol. 48, No. 3, pp. 545-559.

Pearce, L.B., *Pharmacologic Characterization of Botulinum Toxin For Basic Science and Medicine*, Toxicon 35(9);1373-1412 at 1393.

Ragona, *The Laryngoscope* 109:1344-1346:1999.

Sanchez-Prieto, J., et al., *Botulinum Toxin A Blocks Glutamate Exocytosis From Guinea Pig Cerebral Cortical Synaptosomes*, Eur J. Biochem 165;675-681:1897.

Schantz, E.J., et al, *Properties and use of Botulinum toxin and Other Microbial Neurotoxins in Medicine*, Microbiol Rev. 56;80-99:1992.

Senior M., *Botox and the management of pectoral spasm after subpectoral implant insertion*, Plastic and Recon Surg, Jul. 2000, 224-225.

Singh, *Critical Aspects of Bacterial Protein Toxins*, pp. 63-84 (chapter 4) of Natural Toxins II, edited by B.R. Singh et al., Plenum Press, New York (1976).

Sloop, *Neurology*, 48:249-53:1997.

Sneddon P., et al., *Pharamcological evidence that adenosine triphosphate and noradrenaline are cotransmitters in the guinea-pig vas deferens.* J. Physiol. 1984; 347:561-580.

Sulaiman H, et al., *Adhesions have feeling*, Amer J. Gastroenterology, 97(1):9, Jan. 2002.

Sulaiman, H. et al, *Presence and distribution of sensory nerve fibers in human peritoneal adhesions*, Annuals of Surgery, 234(2), Aug. 2001.

Weibel, M.A., et al., *Peritoneal adhesions and their relation to abdominal surgery. A postmortem study*, Amer. J. Surgery, 126, 345-353 (1973).

Weigand et al, *Naunyn-Schmiedeberg's Arch. Pharmacol.* 1976; 292, 161-165.

Xu Z-QD et al, Galanin/GMAP- and NPY-like immunoreactivities in locus coeruleus and noradrenergic nerve terminals in the hippocampal formation and cortex with notes on the galanin-R1 and—R2 receptors, J. Comp. Neurol. 1998; 392: 227-252.

Xu Z-QD et al, *Galanin-5-hydroxytryptamine interactions: Electrophysiological, immunohistochemical and in situ hybridization studies on rat dorsal raphe neurons with a note on galanin R1 and R2 receptors.* Neuroscience 1998; 87: 79-94.

\* cited by examiner

METHOD FOR TREATING PERITONEAL ADHESIONS

BACKGROUND

The present invention relates to methods for treating peritoneal adhesions. In particular the present invention relates to methods for treating peritoneal adhesions by administration of a Clostridial neurotoxin, such as a botulinum toxin, to a patient.

Peritoneal Adhesions

Internal organs, such as the stomach, most of the intestine, parts of the female reproductive system and the inside of the abdominal wall are typically covered with a shiny membrane called the peritoneum. A film of fluid called peritoneal fluid coats adjacent layers of peritoneum. The peritoneum and the peritoneal fluid essentially lubricate internal organs and permits them to slip and slide in relation to each other during for example digestion when waves of muscular contraction pass along the gut wall and propel the food within the lumen of the gastrointestinal tract.

Injury to the peritoneum, as can occur due to trauma, surgery, infection and/or inflammation can cause the peritoneum to become sticky and to attach itself to other areas of peritoneum, that is peritoneal adhesions can form. Briefly, peritoneal adhesions are pathological fibrotic bands developing after mesothelial damage. Peritoneal adhesions can be a transient phenomenon, followed after a few days by separation, or they can become a permanent adhesion complete with fibrous scar tissue. The formation of peritoneal adhesions can interfere with normal functions, and can cause pain, intestinal obstruction, and infertility.

There are various types of peritoneal adhesions. For example, pelvic adhesions can occur due to a pelvic inflammatory disease. Vascular adhesions can lie between the omentum (a layer of fatty tissue surrounding the intestines) and the area under the left groin. Peritoneal adhesions can occur between the intestines and the top of the abdomen. Additionally, peritoneal adhesions can occur between the liver and the diaphragm ("violin string" adhesions)

Peritoneal adhesions can occur in response to peritoneal injury and can occur as a result of endometriosis (the spread of endometrial tissue from the lining of the uterus out into the peritoneal cavity), and infections producing peritonitis. But most peritoneal adhesions are the result of procedures that involve handling and incisions made during abdominal surgery. Thus, patients who have never had abdominal surgery have perhaps a 10% chance of developing peritoneal adhesions, while about two thirds of patients who have had an abdominal surgery develop adhesions (Weibel, M. A., et al., *Peritoneal adhesions and their relation to abdominal surgery. A postmortem study*, Amer. J. Surgery, 126, 345-353 (1973)) and patients who have had two or more abdominal procedures have about a 93% chance of developing peritoneal adhesions. Menzies, D., et al., *Intestinal obstruction from adhesions— how big is the problem?*, Annals of the Royal College of Surgeons, England, 72, 60-63 (1990).

Adhesion formation is of major concern to the pelvic surgeon. For example, adhesions can be induced when operating on myomas and endometriosis. Most patients develop postoperative adhesions regardless of whether the mode of access to the abdominal cavity is by laparoscopy or laparotomy. Significantly, infertility is related to adhesions in the pelvis in 15-20% of cases. Additionally, peritoneal adhesions are the main cause of mechanical bowel obstruction in 65-80% of cases and contribute to a large extent to health-care expenditures.

There are at least three important consequences of peritoneal adhesions. First, peritoneal adhesions can cause chronic abdominal pain. The pain experienced may be due to traction (pulling) of nerves, distention of an obstructed part of the intestines, and/or the restrictions adhesions place upon organ movement, and the resulting stretching and pulling of smooth muscle of adjacent viscera and/or of the abdominal wall itself. Patients with peritoeneal adhesions often report tenderness at or in the area of the adhesions, indicating that the adhesions themselves can generate pain stimuli. Additionally, it has been reported that sensory nerve fibers presumably capable of nocicoception are present in human peritoneal adhesions. Sulaiman, H. et al, *Presence and distribution of sensory nerve fibers in human peritoneal adhesions*, Annuals of Surgery, 234(2), August 2001, and; Sulaiman H, et al., *Adhesions have feeling*, Amer J. Gastroenterology, 97(1):9, January 2002.

Second, peritoeneal adhesions can cause intestinal obstructions. For example, two thirds of all cases of small bowel obstruction involve peritoneal adhesions. Ellis, H., The clinical significance of adhesions: focus on intestinal obstruction. *European Journal of Surgery*, Suppl (577), 5-9 (1997). Third, adhesions involving the ovaries and fallopian tubes can cause infertility and dyspareunia (painful intercourse).

Adhesiolysis (cutting of adhesions) has been used to treat painful peritoneal adhesions, but has a high risk of the development of new adhesions. For example, when adhesions were cut to relieve intestinal obstruction, obstruction recurs in up to one-fifth of all cases.

Various methods have been tried to reduce the risk of peritoneal adhesion formation. For example, different types of biodegradable or non-biodegradable synthetic membrane (barrier) products can be placed over damaged peritoneum during an operation with the aim of preventing the formation of adhesions. Examples of such products are INTERCEED® (Johnson & Johnson), SEPRAFILM® (Genzyme Corp) and Gore-Tex. Drawbacks of synthetic membrane products can include lack of absorption, occurrence of inflammation, requirement for suturing or stapling to hold the membrane in place, and formation of new peritoneal adhesions after laparoscopy. Other medications that have been studied to try and prevent the occurrence of postoperative peritoneal adhesions include glucocorticoids, heparin, dextran 70, saline solution, antibiotics, promethazine, antihistamines, prostaglandin synthesis inhibitors, Ringer's lactate solution and calcium-channel blockers.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)1 is a LD50 in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated LD50 of botulinum toxin type A of 0.3 ng equals 1 U is corrected for the fact that about 0.05 ng of BOTOX® equals 1 unit). One unit (U) of botulinum toxin is defined as the LD50 upon intraperitoneal injection into female Swiss Webster mice weighing 18 to 20 grams each.

Seven generally immunologically distinct botulinum neurotoxins have been characterized, these being respectively botulinum neurotoxin serotypes A, B, C1, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate LD50 for botulinum toxin type A. Moyer E et al., *Botulinum Toxin Type B: Experimental and Clinical Experience*, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, HC, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane.

Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype C1 was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989, a botulinum toxin type A complex has been approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type C1 has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem J* 1;339 (pt 1):159-65:1999, and *Mov Disord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and C1 is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2);522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675-681:1897. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9);1373-1412 at 1393; Bigalke H., et al., *Botulinum A Neurotoxin Inhibits Non-Cholinergic Synaptic Transmission in Mouse Spinal Cord Neurons in Culture*, Brain Research 360;318-324:1985; Habermann E., *Inhibition by Tetanus and Botulinum A Toxin of the release of [3H]Noradrenaline and [3H]GABA From Rat Brain Homogenate*, Experientia 44;224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes C1, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geqq 3 \times 10^7$ U/mg, an A260/A278 of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine*, Microbiol Rev. 56;80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of 1-2$\times 10^8$ LD50 U/mg or greater; purified botulinum toxin type B with an approximately 156 kD molecular weight with a specific potency of 1-2$\times 10^8$ LD50 U/mg or greater, and; purified botulinum toxin type F with an approximately 155 kD molecular weight with a specific potency of 1-2$\times 10^7$ LD50 U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX®D contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249-53:1997.

It has been reported that botulinum toxin type A has been used in clinical settings as follows:
(1) about 75-125 units of BOTOX® per intramuscular injection (multiple muscles) to treat cervical dystonia;
(2) 5-10 units of BOTOX® per intramuscular injection to treat glabellar lines (brow furrows) (5 units injected intramuscularly into the procerus muscle and 10 units injected intramuscularly into each corrugator supercilii muscle);
(3) about 30-80 units of BOTOX® to treat constipation by intrasphincter injection of the puborectalis muscle;
(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).
(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.
(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (European J. Neurology 6 (Supp 4): S111-S1150:1999), and in some circumstances for as long as 27 months, when used to treat glands, such as in the treatment of hyperhydrosis. See e.g. Bushara K., Botulinum toxin and rhinorrhea, Otolaryngol Head Neck Surg 1996; 114(3):507, and The Laryngoscope 109:1344-1346:1999. However, the usual duration of an intramuscular injection of BOTOX® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and DYSPORT® available from Beaufour Ipsen, Porton Down, England. A Botulinum toxin type B preparation (MYOBLOC®)) is available from Elan Pharmaceuticals of San Francisco, Calif.

In addition to having pharmacologic actions at the peripheral location, botulinum toxins may also have inhibitory effects in the central nervous system. Work by Weigand et al, *Nauny-Schmiedeberg's Arch. Pharmacol.* 1976; 292, 161-165, and Habermann, *Nauny-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

Significantly, it has been reported that local administration of a botulinum toxin can cause the development of certain esophageal adhesions: Gordon J. M., et al., *Prospective study of esophageal botulinum toxin injection in high-risk achalasia patients*, Am J Gastroenterol 1997 October;92(10): 1812-7 1012 (development of mediastinal adhesions around the distal esophagus after botulinum toxin injection); Eaker E. Y., et al., *Untoward effects of esophageal botulinum toxin injection in the treatment of achalasia*, Dig Dis Sci 1997 April;42(4):724-7 1012 (development of paresophageal adhesions after botulinum toxin injection), and; Bhutani M. S., et al., *Botulinum toxin injection in achalasia before myotomy*, Am J Gastroenterol 1998 June;93(6):1012 (development of paresophageal adhesions after botulinum toxin injection).

Additionally, a botulinum toxin has been proposed for or has been used to treat skin bone and tendon wounds (U.S. Pat. No. 6,447,787); intrathecal pain (see e.g. U.S. Pat. No. 6,113, 915); various autonomic nerve disorders, including sweat gland disorders (see e.g. U.S. Pat. No. 5,766,605 and Goldman (2000), Aesthetic Plastic Surgery July-August 24(4): 280-282); tension headache (U.S. Pat. No. 6,458,365); migraine headache pain (U.S. Pat. No. 5,714,468); post-operative pain and visceral pain (U.S. Pat. No. 6,464,986); hair growth and hair retention (U.S. Pat. No. 6,299,893); psoriasis and dermatitis (U.S. Pat. No. 5,670,484); injured muscles (U.S. Pat. No. 6,423,319); various cancers (see e.g. U.S. Pat. Nos. 6,139,845 and 6,063,768), smooth muscle disorders (U.S. Pat. No. 5,437,291); nerve entrapment syndromes (U.S. patent application 2003 0224019); acne (WO 03/011333); neurogenic inflammation (U.S. Pat. No. 6,063,768); otic disorders (see e.g. U.S. Pat. No. 6,265,379); pancreatic disorders (see e.g. U.S. Pat. Nos. 6,143,306 and 6,261,572); prostate disorders, including prostatic hyperplasia, prostate cancer and urinary incontinence (see e.g. U.S. Pat. Nos. 6,365,164 and 6,667,041 [which also disclose treatment of pelvic pain] and Doggweiler R., et al *Botulinum toxin type A causes diffuse and highly selective atrophy of rat prostate*, Neurourol Urodyn 1998; 17(4):363); fibromyalgia (U.S. Pat. No. 6,623, 742); piriformis muscle syndrome (see e.g. Childers et al. (2002), American Journal of Physical Medicine & Rehabilitation, 81:751-759); and various skin disorders (see U.S. patent applications serial numbers 731,973; 814,764, and; 817,036).

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord. Additionally it has been disclosed that targeted botulinum toxins (i.e. with a non-native binding moiety) can be used to treat various conditions (see e.g. WO 96/33273; WO 99/17806; WO 98/07864; WO 00/57897; WO 01/21213; WO 00/10598.

A botulinum toxin has been injected into the pectoral muscle to control pectoral spasm. See e.g. Senior M., *Botox and the management of pectoral spasm after subpectoral implant insertion*, Plastic and Recon Surg, July 2000, 224-225. Controlled release toxin implants are known (see e.g. U.S. Pat. Nos. 6,306,423 and 6,312,708) as is transdermal botulinum toxin administration (U.S. patent application Ser. No. 10/194,805).

Both liquid stable formulations and pure botulinum toxin formulations have been disclosed (see e.g. WO 00/15245 and WO 74703) as well as topical application of a botulinum toxin (see e.g. DE 198 52 981).

Additionally, a botulinum toxin may have an effect to reduce induced inflammatory pain in a rat formalin model. Aoki K., et al, *Mechanisms of the antinociceptive effect of subcutaneous Botox: Inhibition of peripheral and central nociceptive processing*, Cephalalgia 2003 September;23(7): 649.

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16);9153-9158: 1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is a therapeutically effective method for treating an adhesion, such as a peritoneal adhesion.

SUMMARY

The present invention meets this need and provides methods for effectively treating a peritoneal adhesion by local administration of a Clostridial neurotoxin.

A method within the scope of the present invention for treating a peritoneal adhesion can have the step of local administration of a Clostridial neurotoxin to a location of a peritoneal adhesion of a patient, such as to an intra-abdominal location. By local administration it is meant that the Clostridial neurotoxin (such as a botulinum neurotoxin) is administered, as by injection, directly to, in, or to the vicinity of, a region of a peritoneal adhesion. The neurotoxin can be locally administered in an amount of between about $10^{-3}$ units/kg of patient weight and about 35 units/kg of patient weight. Preferably, the neurotoxin is locally administered in an amount of between about $10^{-2}$ U/kg and about 25 U/kg of patient weight. More preferably, the neurotoxin is administered in an amount of between about $10^{-1}$ U/kg and about 15 U/kg. In a particularly preferred method within the scope of the present invention, the neurotoxin is locally administered in an amount of between about 1 U/kg and about 10 U/kg. In a clinical setting it can be advantageous to inject from 1 U to 3000 U of a neurotoxin, such as botulinum toxin type A or B, to a peritoneal adhesion location by topical application or by intra-abdominal administration, to effectively treat the peritoneal adhesion.

A suitable neurotoxin for use in the practice of the present invention can be made by a Clostridial bacterium, such as *Clostridium botulinum, Clostridium butyricum* or *Clostridium beratti*. The neurotoxin use can be a modified neurotoxin that is a neurotoxin has had at least one of its amino acids deleted, modified or replaced, as compared to a native neurotoxin. Additionally, the neurotoxin can be recombinantly made produced neurotoxin or a derivative or fragment of a recombinant made neurotoxin. The neurotoxin can be a botulinum toxin, such as one of the botulinum toxin serotypes A, B, $C_1$, D, E, F or G. A preferred botulinum toxin to use in the practice of the present invention is botulinum toxin type A.

A method according to my invention can be carried out by administration of a Clostridial toxin to a patient with, or who is predisposed to, development of a peritoneal adhesion. The Clostridial toxin used is preferably a botulinum toxin (as either a complex or as a pure [i.e. about 150 kDa molecule], such as a botulinum toxin A, B, C, D, E, F or G. Administration of the Clostridial toxin can be by an intravaginal or trans-abdominal route of administration.

The dose of a Clostridial toxin used according to the present invention is less than the amount of toxin that would be used to paralyze a muscle, since the intent of a method according to the present invention is not to paralyze a muscle but to treat a peritoneal adhesion.

The following definitions apply herein:

"About" means approximately or nearly and in the context of a numerical value or range set forth herein means ±10% of the numerical value or range recited or claimed.

An "adhesion" is a fibrotic band that develops after mesothelial damage.

"Alleviating" means a reduction in the prominence of a peritoneal adhesion. Thus, alleviating includes some reduction, significant reduction, near total reduction, and total reduction of a peritoneal adhesion. An alleviating effect may not appear clinically for between 1 to 7 days after administration of a Clostridial neurotoxin to a patient.

"Botulinum toxin" means a botulinum neurotoxin as either pure toxin (i.e. about 150 kDa weight molecule) or as a complex (i.e. about 300 to about 900 kDa weight complex comprising a neurotoxin molecule and one or more associated non-toxic molecules), and excludes botulinum toxins which are not neurotoxins such as the cytotoxic botulinum toxins C2 and C3, but includes recombinantly made, hybrid, modified, and chimeric botulinum toxins.

"Local administration" or "locally administering" means administration (i.e. by an intravaginal or transabdominal route) of a pharmaceutical agent to or to the vicinity of a peritoneal adhesion.

"Treating" means to alleviate (or to eliminate) at least one symptom of a peritoneal adhesion (such as pain), either temporarily or permanently.

The Clostridial neurotoxin is administered in a therapeutically effective amount to alleviate a symptom of a peritoneal adhesion. A suitable Clostridial neurotoxin may be a neurotoxin made by a bacterium, for example, the neurotoxin may be made from a *Clostridium botulinum, Clostridium butyricum*, or *Clostridium beratti*. In certain embodiments of the invention, the peritoneal adhesion can be treated by applying to (topical) or into (intra or transdermal) the abdomen of a patient a botulinum toxin. The botulinum toxin can be a botulinum toxin type A, type B, type C1, type D, type E, type F, or type G. The peritoneal adhesion alleviating effects of the botulinum toxin may persist for between about 2 weeks (i.e. upon administration of a short acting botulinum toxin, such as a botulinum toxin type E) and 5 years (i.e. upon implantation of a controlled release botulinum toxin implant). The botulinum neurotoxin can be a recombinantly made botulinum neurotoxins, such as botulinum toxins produced by an *E. coli* bacterium. In addition or alternatively, the botulinum neurotoxin can be a modified neurotoxin, that is a botulinum neurotoxin which has at least one of its amino acids deleted, modified or replaced, as compared to a native or the modified botulinum neurotoxin can be a recombinant produced botulinum neurotoxin or a derivative or fragment thereof.

A method for treating a peritoneal adhesion according to the present invention can comprise the step of local administration of a botulinum toxin to a patient with a peritoneal adhesion to thereby alleviate the peritoneal adhesion. The botulinum toxin can be selected from the group consisting of botulinum toxin types A, B, C, D, E, F and G. Botulinum toxin type A is a preferred botulinum toxin.

A detailed embodiment of my invention can comprise a method for treating a peritoneal adhesion by local administration to a patient with a peritoneal adhesion of between about 1 unit and about 3,000 units of a botulinum toxin (for example between about 1-300 units of a botulinum toxin type A or between about 50 to 15,000 units of a botulinum toxin type B), thereby alleviating the peritoneal adhesion for between about two weeks and about 5 years.

My invention also encompasses a method for treating peritoneal adhesion by locally administering a botulinum toxin (such as a botulinum toxin type A, B, C, D, E, F or G, in an amount of from 1 unit to 15,000 units per treatment session) to a patient predisposed to develop peritoneal adhesions, thereby preventing the patient from developing a peritoneal adhesion. A patient predisposed to peritoneal adhesion is a human who has developed a peritoneal adhesion at least once within the last twelve months. The peritoneal adhesion can be reduced in size by from about 20% to 100%.

DESCRIPTION

The present invention is based upon the discovery that a peritoneal adhesion can be treated by local administration of a therapeutically effective amount of a Clostridial neurotoxin, such as a botulinum neurotoxin. The botulinum neurotoxin (such as a botulinum neurotoxin serotype A, B, $C_1$ D, E, F or G) can be injected into or topically applied (onto the outer or inner abdominal wall or the affected viscera) onto or in the vicinity of a peritoneal adhesion of a patient. Alternately, the botulinum toxin can be administered to an intradermal or subdermal neuron to thereby downregulate, inhibit or suppress a neuronally mediated or influenced peritoneal adhesion.

The present invention encompasses methods for the treatment of peritoneal adhesions, including methods for the treatment of the pain that can be associated with peritoneal adhesions, using a therapeutically effective amount of a botulinum toxin. The botulinum toxin can be delivered or applied directly to a peritoneal adhesion(s) and/or to the abdominal smooth musculature and or viscera to which the adhesion or adhesions are adhering to, resulting in a decrease in tension (stretching and pulling) of both the muscle abdominal wall and/or viscera within the affected structure as well as directly reducing neuropeptide release from the sensory nerves found innervating the adhesion or adhesions.

Without wishing to be bound by theory it can be hypothesized that use of a botulinum toxin by the methods set forth herein may have efficacy for the treatment of peritoneal adhesions due to: (1) a relaxation of the muscle tissue, thereby decreasing tension or elasticity (adherence) of the adhesion, and therefore resulting in a reduction of pain fiber activation, and; (2) a direct effect upon pain fibers to reduce transmission of pain signal by the structure affected by the adhesion.

Methods within the scope of the present invention have the important feature of being practised so as to prevent or so as to substantially prevent or avoid the spread of the botulinum toxin and/or the effects of the botulinum toxin beyond the area of the abdomen or perineum afflicted by the peritoneal adhesions.

Any suitable method for local administration of a botulinum toxin to treat a peritoneal adhesion is within the scope of the present invention. For example, a botulinum toxin can be delivered to a peritoneal adhesion or to the vicinity of a peritoneal adhesion by a trans-abdominal or intravaginal route.

Examples of methods within the scope of the present invention for treating a peritoneal adhesion by local administration of a botulinum toxin to an appropriate location (such as to the afflicted abdominal wall) can include:

(1) intravaginal delivery, with ultrasound or fluoroscopy guidance, of an adsorbent or absorbent material such as a biocompatible, and preferably bioerodible, contraceptive sponge material, instilled or coated with an effective amount of a botulinum toxin;

(2) intravesical instillation of a botulinum toxin solution into the abdominal cavity. See e.g. Chancellor M. B., et al., Intravesical botulinum toxin A administration produces analgesia against acetic acid induced bladder pain responses in rats, J Urol 2004 April;171(4 Suppl);

(3) trans-abdominal injection with fluoroscopy, or MRI or other guidance, and;

(4) endoscopically with guidance (Fluoroscopy, or US, or CT, or MRI).

Without wishing to be bound by theory a physiological mechanism can be proposed for the efficacy of my invention as disclosed herein for the treatment of a peritoneal adhesion using a Clostridial neurotoxin. Essentially, it is hypothesized that use of a botulinum toxin can inhibit release of acetylcholine and/or of another neurotransmitter or neuropeptide by one or more nerves or structures which innervate or which influence a peritoneal adhesion, to thereby permit effective treatment of a peritoneal adhesion. Alternately, the administered Clostridial neurotoxin may have a direct effect upon the peritoneal adhesion. By effective treatment it is meant that the peritoneal adhesion becomes less painful, less inflammed and/or regresses (i.e. becomes smaller in size [i.e. thinner] or disappears altogether).

Thus, it can be postulated that a botulinum toxin can be used to induce denervation and thereby can treat a peritoneal adhesion—by preventing (i.e. downregulating) the release of various neuropeptides released by nerves which innervate the adhesion. Among these neuropeptides are the tachykinins, substance P and neurokinin A, calcitonin gene-related peptide (CGRP), vasoactive intestinal peptide (VIP) and somatostatin, one or more of which may modulate cell functions such as adhesion cell proliferation. As set forth previously, release of most neurotransmitters and related neuropeptides can be blocked by botulinum toxin. See e.g. Hokfelt T., *Neuropeptides in perspective: The last ten years*, Neuron 1991; 7: 867-879; Xu Z-QD et al, *Galanin/GMAP- and NPY-like immunoreactivities in locus coeruleus and noradrenergic nerve terminals in the hippocampal formation and cortex with notes on the galanin-R1 and -R2 receptors*, J. Comp. Neurol. 1998; 392: 227-252; Xu Z-Q D et al, *Galanin-5-hydroxytryptamine interactions: Electrophysiological, immunohistochemical and in situ hybridization studies on rat dorsal raphe neurons with a note on galanin R1 and R2 receptors*. Neuroscience 1998; 87: 79-94; Johnson M., *Synaptic glutamate release by postnatal rat serotonergic neurons in microculture*, Neuron 1994; 12: 433-442; Sneddon P., et al., *Pharamcological evidence that adenosine triphosphate and noradrenaline are cotransmitters in the guinea-pig vas deferens*. J. Physiol. 1984; 347: 561-580; Kaneko T., et al., *Immunohistochemical demonstration of glutaminase in catecholaminergic and serotonergic neurons of rat brain*, Brain Res. 1990; 507: 141-154; Kasakov L., et al., *Direct evidence for concomitant release of noradrenaline, adenosine 5'-triphosphate and neuropeptide Y from sympathetic nerve supplying the guinea-pig vas deferens*. J. Auton. Nerv. Syst. 1988; 22: 75-82; Nicholas A. et al., *Glutamate-like immunoreactivity in medulla oblongata catecholaminelsubstance P neurons*, NeuroReport 1990; 1: 235-238; Nicholas A. et al., Kupfermann I., *Functional studies of cotransmission*. Physiol. Rev. 1991; 71: 683-732.48: 545-59; Lundberg J., *Pharmacology of cotransmission in the autonomic nervous system: Integrative aspects on amines, neuropeptides, adenosine triphosphate, amino acids and nitric oxide*, Pharmacol. Rev. 1996; 48: 113-178; Hsieh S., et al., *Skin Innervation and Its Effects on the Epidermis*, J Biomed Sci. 1997;4(5):264-268; Legat F., et al., *Repeated subinflammatory ultraviolet B irradiation increases substance P and calcitonin gene-related peptide content and augments mustard oil-induced neurogenic inflammation in the skin of rats*, Neurosci Lett. 2002 Sep. 6;329(3):309-13; White S., et al., Asahina A., et al., *Specific induction of cAMP in Langerhans cells by calcitonin gene-related peptide: relevance to functional effects*, Proc Natl Acad Sci USA. 1995 Aug. 29;92(18):8323-7; Inaba N., et al., *Capsaicin-induced calcitonin gene-related peptide release* from isolated rat stomach measured with a new chemiluminescent enzyme immunoassay, Jpn J Pharmacol. 1996 November;72(3):223-9; Hosoi J., et al., *Regulation of Langerhans cell function by nerves containing calcitonin gene-related peptide*, Nature. 1993 May 13;363(6425):159-63.

The amount of the Clostridial toxin administered according to a method within the scope of the disclosed invention can vary according to the particular characteristics of the peritoneal adhesion being treated, including its severity and other various patient variables including size, weight, age, and responsiveness to therapy. To guide the practitioner, typically, no less than about 1 unit and no more than about 300 units of a botulinum toxin type A (such as BOTOX®) is administered per injection site (i.e. to each peritoneal adhesion location injected), per patent treatment session. For a botulinum toxin type A such as DYSPORT®, no less than about 2 units and no more about 1200 units of the botulinum toxin type A are administered per administration or injection site, per patent treatment session. For a botulinum toxin type B such as MYOBLOC®, no less than about 40 units and no more about 1500 units of the botulinum toxin type B are administered per administer or injection site, per patent treatment session. Less than about 1, 2 or 40 units (of BOTOX®, DYSPORT® and MYOBLOC® respectively) can fail to achieve a desired therapeutic effect, while more than about 300, 1200 or 15000 units (of BOTOX®, DYSPORT® and MYOBLOC® respectively) can result in clinically observable and undesired muscle hypotonicity, weakness and/or paralysis.

More preferably: for BOTOX® no less than about 2 units and no more about 150 units of a botulinum toxin type A; for DYSPORT® no less than about 4 units and no more than about 600 units, and; for MYOBLOC®, no less than about 80 units and no more than about 7500 units are, respectively, administered per injection site, per patent treatment session.

Most preferably: for BOTOX® no less than about 5 units and no more about 100 units of a botulinum toxin type A; for DYSPORT® no less than about 20 units and no more than about 400 units, and; for MYOBLOC®, no less than about 200 units and no more than about 5000 units are, respectively, administered per injection site, per patent treatment session. It is important to note that there can be multiple injection sites (i.e. a pattern of injections) for each patient treatment session.

The present invention is based on the discovery that local administration of a Clostridial toxin can provide significant and long lasting relief from a peritoneal adhesion. A Clostridial toxin used in accordance with the invention disclosed herein can inhibit transmission of chemical or electrical signals between select neuronal groups that are involved in generation of a peritoneal adhesion. The Clostridial toxins preferably are not cytotoxic to the cells that are exposed to the Clostridial toxin. The Clostridial toxin can inhibit neurotransmission by reducing or preventing exocytosis of neurotransmitter from the neurons exposed to the Clostridial toxin. Or the applied Clostridial toxin can reduce neurotransmission by inhibiting the generation of action potentials of the neurons exposed to the toxin. The peritoneal adhesion alleviation effect provided by the Clostridial toxin can persist for a relatively long period of time, for example, for more than two months, and potentially for several years.

Examples of Clostridial toxins within the scope of the present invention include neurotoxins made by *Clostridium botulinum*, *Clostridium butyricum* and *Clostridium beratti* species. In addition, the botulinum toxins used in the methods of the invention may be a botulinum toxin selected from a group of botulinum toxin types A, B, C, D, E, F, and G. In one embodiment of the invention, the botulinum neurotoxin administered to the patient is botulinum toxin type A. Botulinum toxin type A is desirable due to its high potency in humans, ready availability, and known use for the treatment of skeletal and smooth muscle disorders when locally administered by intramuscular injection. The present invention also includes the use of (a) Clostridial neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Although the composition may only contain a single type of neurotoxin, such as botulinum toxin type A, as the active ingredient to suppress neurotransmission, other therapeutic compositions may include two or more types of neurotoxins, which may provide enhanced therapeutic treatment of a peritoneal adhesion. For example, a composition administered to a patient may include botulinum toxin type A and botulinum toxin type B. Administering a single composition containing two different neurotoxins can permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the GABM receptor. The GABAA receptor inhibits neuronal activity by effectively shunting current flow across the cell membrane. GABAA receptor modulators may enhance the inhibitory effects of the GABAA receptor and reduce electrical or chemical signal transmission from the neurons. Examples of GABAA receptor modulators include benzodiazepines, such as diazepam, oxaxepam, lorazepam, prazepam, alprazolam, halazeapam, chordiazepoxide, and chlorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat a peritoneal adhesion can include one or more neurotoxins, such as botulinum toxins, in addition to ion channel receptor modulators that may reduce neurotransmission.

The neurotoxin may be administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a botulinum toxin within a tissue appears to be a function of dose and can be graduated. Jankovic J., et al *Therapy With Botulinum Toxin*, Marcel Dekker, Inc., (1994), page 150. Thus, diffusion of botulinum toxin can be controlled to reduce potentially undesirable side effects that may affect the patient's cognitive abilities. For example, the neurotoxin can be administered so that the neurotoxin primarily effects neural systems believed to be involved in the generation of a peritoneal adhesion.

A polyanhydride polymer, Gliadel® (Stolle R & D, Inc., Cincinnati, Ohio) a copolymer of poly-carboxyphenoxypropane and sebacic acid in a ratio of 20:80 has been used to make implants, and has been intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al, *Placebo-Controlled Trial of Safety and Efficacy of Intraoperative Controlled Delivery by Biodegradable Polymers of Chemotherapy for Recurrent Gliomas*, Lancet 345;1008-1012:1995.

Implants useful in practicing the methods disclosed herein may be prepared by mixing a desired amount of a stabilized neurotoxin (such as non-reconstituted BOTOX®) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58;672-684:1998.

Local administration of a Clostridial toxin, such as a botulinum toxin, can provide a high, local therapeutic level of the toxin. A controlled release polymer capable of long term, local delivery of a Clostridial toxin to a target peritoneal adhesion location permits effective dosing of the target tissue. A suitable implant, as set forth in U.S. Pat. No. 6,306,423 entitled "Neurotoxin Implant", allows the direct introduction of a chemotherapeutic agent to a target tissue via a controlled release polymer. The implant polymers used are preferably hydrophobic so as to protect the polymer incorporated neurotoxin from water induced decomposition until the toxin is released into the target tissue environment.

Local administration of a botulinum toxin, according to the present invention, by injection or implant to a target tissue provides a superior alternative to systemic administration of pharmaceuticals to patients to alleviate a peritoneal adhesion.

The amount of a Clostridial toxin selected for local administration to a target tissue according to the present disclosed invention can be varied based upon criteria such as the severity of the peritoneal adhesion being treated, solubility characteristics of the neurotoxin toxin chosen as well as the age, sex, weight and health of the patient. For example, the extent of the area of an adhesion influenced is believed to be proportional to the volume of neurotoxin injected, while the quantity of the peritoneal adhesion suppressant effect is, for most dose ranges, believed to be proportional to the concentration of a Clostridial toxin administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill).

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality and general health perceptions. Scores obtained can be compared to published values available for various general and patient populations.

EXAMPLES

The following non-limiting examples provide those of ordinary skill in the art with specific preferred methods to treat conditions within the scope of the present invention and are not intended to limit the scope of the invention. In the following examples various modes of non-systemic administration of a Clostridial neurotoxin can be carried out. For example, by topical application to an adhesion, intravaginal, transabdominally, implantation of a controlled release implant or injection into or into the local area of an adhesion.

Example 1

Use of a Botulinum Toxin to Treat Peritoneal Adhesions Causing Abdominal Pain

A twenty five year old female presents complaining of a three week period of abdominal pain localized to the lower-mid abdominal region on the right side. Upon examination, patient retracts upon palpation of the affected area which is clearly tender. She reports an increased frequency of sexual intercourse beginning about one year ago. About 6 months ago, the patient is treated for an STD (sexually transmitted disease, probably bacterial vaginosis). Results of an ultrasound reveal adhesions about three inches long spanning the lower abdominal wall to parts of the large and small intestine.

The patient, given her history, ultrasound results, and symptoms upon presentation, is diagnosed with pelvic inflammatory disease probably secondary to a recent STD.

Following a course of anti-inflammatory medications, the patient still has persistent pain. A series of other analgesics are tried with no effect on the pain, described as an "8-9" on a scale of 0-10. Given the lack of efficacy in previous treatments, and continual pain, a course of intravaginal botulinum toxin is chosen with the patient's consent. 100 units of a botulinum toxin type A (BOTOX®; alternately about 400 units of DYSPORT® or about 5000 units of MYOBLOC® can be used) is reconstituted with 1 ml saline solution (for MYOBLOC® reconstitution is not necessary) and is applied to an absorbent sponge that is administered via intravaginally, under ultrasound guidance directly to the adhesive structure as well as to the abdominal wall in the region of the adhesions. At follow-up one month later, the patient notes significant improvement in her pain; from an 8-9 scale rating prior to treatment to a 2-3 scale rating. Another botulinum toxin administration is carried out three months after her first botulinum toxin treatment. One month after her second botulinum toxin treatment the patient reports her pain reduced to a 1-2 scale rating, and note an improvement in her physical activity as well.

Example 2

Use of a Botulinum Toxin to Treat Peritoneal Adhesions Secondary to Surgery

A 38 year old woman thought to have bilateral polycystic ovaries and an absence of pelvic or abdominal adhesions at diagnostic laparoscopy. Post-operative transvaginal ultrasound notes bilateral homogeneous hypo-echoic masses with low-level echoes consistent with endometriomas. Transvaginal aspiration is unsuccessful due to the viscosity of the cyst contents. At second laparoscopy severe adhesions with complete cul-de-sac obliteration are noted. Due to the extensive nature of adhesions and history of surgeries which also appears to stimulate adhesion formation, an non-invasive trial of botulinum toxin is initiated. 200 units of a botulinum toxin type A (BOTOX®; alternately about 400 units of DYSPORT® or about 5000 units of MYOBLOC® can be used) was reconstituted with 1 ml saline solution (for MYOBLOC® reconstitution is not necessary) and was applied to an absorbent sponge that is administered via intravaginally to the affected regions including the superficial surface of the ovaries, abdominal wall, and directly to the adhesions. Follow-up one month later reveals a reduction of adhesions via ultrasound, and the patient notes significant improvement in pain and tenderness.

Example 3

Laparoscopic Administration of a Botulinum Toxin to Treat Peritoneal Adhesions

A 53-year-old woman is admitted with respiratory distress. For several years, she has had chronic alcoholic pancreatitis with ductal stones that were treated with a stent and with shockwave lithotripsy. Both treatments are unsuccessful, and the pancreatitis is complicated with an infected pseudocyst. The pancreatic head is resected, which is complicated with recurrent subphrenic abscesses. She is then admitted with respiratory distress and initially diagnosed with pneumonia of the right lower lobe. Further investigations show supradiaphragmatic and subdiaphragmatic air-fluid levels. In both collections Streptococcus milleri was cultured, and subsequently the patient is diagnosed with a fistula connecting the subdiaphragmatic abscess with pulmonary tissue. This is treated with intravenous amoxicillin/clavulanate and drainage of the subdiaphragmatic collection. She does not develop a pulmonary empyema, because multiple adhesions, which were due to recurrent abscesses after pancreatic surgery, prevent breakthrough into the pleural cavity. But the adhesions create a chronic abdominal pain for her. Hence, 75 units of a botulinum toxin type A (BOTOX®) is injected laparoscopically over five locations at the site from which she reports the pain to originate. Within 2-7 days her pain is substantially reduced.

In each of the examples above a botulinum toxin type B, C, D, E, F or G can be substituted for the botulinum toxin type A used above, for example by use of 3000-5000 units of a botulinum toxin type B. The specific amount of a botulinum toxin (such as BOTOX®) administered depends upon a variety of factors to be weighed and considered within the discretion of the attending physician and in each of the examples insignificant amounts of botulinum toxin enter appear systemically with no significant side effects.

A method for treating a peritoneal adhesion according to the invention disclosed herein has many benefits and advantages, including the following:

1. peritoneal adhesions can be dramatically reduced or eliminated.

2. the peritoneal adhesion can be reduced or eliminated for at least about two weeks to about six months per injection of neurotoxin and for from about one year to about five years upon use of a controlled release neurotoxin implant.

3. the injected or implanted Clostridial neurotoxin shows little or no tendency to diffuse or to be transported away from the intramuscular (or intradermal or subdermal) injection or implantation site.

4. few or no significant undesirable side effects occur from injection or implantation of the Clostridial neurotoxin.

5. the present methods can result in the desirable side effects of greater patient mobility, a more positive attitude and an improved quality of life.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local administration methods to alleviate a peritoneal adhesion wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type B. Alternately, a combination of any two or more of the botulinum serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect.

A botulinum toxin can be administered by itself or in combination of one or more of the other botulinum toxin serotypes. The botulinum toxin can be a recombinantly made or a hybrid botulinum toxin.

My invention also includes within its scope the use of a neurotoxin, such as a botulinum toxin, in the preparation of a medicament for the treatment of a peritoneal adhesion, by local administration of the neurotoxin.

All references, articles, patents, applications and publications set forth above are incorporated herein by reference in their entireties.

Accordingly, the spirit and scope of the following claims should not be limited to the descriptions of the preferred embodiments set forth above.

I claim:

1. A method for treating a peritoneal adhesion in a patient, the method comprising a step of local administration of a therapeutically effective amount of botulinum toxin to a peritoneal adhesion or to the vicinity of a peritoneal adhesion of said patient, thereby treating the peritoneal adhesion.

2. The method of claim 1, wherein the botulinum toxin is selected from the group consisting of botulinum toxin types A, B, C, D, E, F and G.

3. The method of claim 1, wherein the botulinum toxin is a botulinum toxin type A.

4. The method of claim 1, wherein the botulinum toxin is administered in an amount of between about 1 unit and about 3,000 units.

5. The method of claim 1, wherein the administration is by administration of the botulinum toxin to an abdominal region.

6. A method for treating a peritoneal adhesion in a patient, the method comprising the step of locally administering a therapeutically effective amount between 1 unit and 3000 units of a botulinum toxin to a peritoneal adhesion of the patient, thereby treating the peritoneal adhesion.

7. The method of claim 6, wherein treating the peritoneal adhesion reduces the adhesion of the peritoneal adhesion to the peritoneum or to the viscera.

* * * * *